United States Patent [19]
Paul

[11] Patent Number: 5,865,826
[45] Date of Patent: Feb. 2, 1999

[54] DEVICE AND METHOD FOR WIDENING A HOLLOW BODY HAVING AN AT LEAST PARTIALLY ELASTIC REGION

[76] Inventor: Volker Paul, A.-Weisgerber-Allee 144, D-66386 St. Ingbert, Germany

[21] Appl. No.: 720,066

[22] Filed: Sep. 27, 1996

[30]      Foreign Application Priority Data

Sep. 27, 1995 [DE] Germany ............... 195 35 993.3

[51] Int. Cl.[6] ............................................. A61B 17/00
[52] U.S. Cl. ................................... 606/1; 606/191
[58] Field of Search ..................... 606/1, 106–108, 606/113, 114, 127, 128, 151, 191–200, 201; 600/204, 207, 210; 604/96, 104

[56]           References Cited

U.S. PATENT DOCUMENTS

| 5,122,148 | 6/1992 | Alexander | 606/122 |
|---|---|---|---|
| 5,122,155 | 6/1992 | Eberbach | 606/151 |
| 5,192,284 | 3/1993 | Pleatman | 606/127 |
| 5,352,184 | 10/1994 | Goldberg . | |
| 5,499,988 | 3/1996 | Espiner et al. | 600/37 |

FOREIGN PATENT DOCUMENTS 27 44 260   4/1979   Germany .

Primary Examiner—Glenn K. Dawson

[57]              ABSTRACT

A device for widening a hollow body at least partially having elastic regions, which device is connected to the hollow body and widens the hollow body to a desired circumference. At least one elastic device, which can be concertedly widened over its full length by means of force transmitting means, is disposed on the hollow body.

18 Claims, 5 Drawing Sheets

DEVICE AND METHOD FOR WIDENING A HOLLOW BODY HAVING AN AT LEAST PARTIALLY ELASTIC REGION

BACKGROUND AND SUMMARY OF THE INVENTION

The present invention relates to a device and a method for widening a hollow body having an at least partially elastic region, in which an elastic device is firmly connected to the hollow body to widen the hollow body to a desired circumference.

In certain circumstances, there is a need in medicine to surround with a cover, e.g., to protect against mechanical or chemical influences or for the purpose of locating. Particularly in the field of organology, there is a need in certain cases to protect an organ against exterior chemical or mechanical influences by covering the organ. If these covers fit snugly, e.g. for locating purposes, elastic covers are employed which are widened accordingly before they can be drawn over the organs.

It is known to widen elastic covers from the interior by means of suitable tools or to manually open elastic covers in such a manner that the cover can be slipped over the object to be covered. When the cover slackens and thus contracts, the tools and/or fingers used for widening it reach in between the cover and the object to be covered and are pressed against the object by the contracting force of the cover. Especially if sensitive objects are involved, for example human organs, the contracting force of the cover transmitted through the assisting tools and/or fingers may result in deformations of the organs which can lead to irreversible damage. Moreover, there is also the danger that unevenness or edges of the assisting tools and/or fingers may damage the object to be covered when the contracting pressure is applied.

Once the elastic cover is positioned about the object to be covered in the proper manner and fits, the assisting tools and/or the fingers have to be drawn out from between the cover and the covered object. However, during this drawing out lateral forces act upon the cover and the object. These forces can, on the one hand, cause the object to shift position or the object and the cover to shift position in relation to each other, which on the other hand, may lead to further damage to the cover and to the covered object. The object to be covered is subject to further stress from jolting when the assisting tools and/or the fingers are ultimately withdrawn caused by the elasticity of the cover, i.e., a snapping down effect of the elastic cover against the object to be covered when the assisting tools and/or the fingers are finally fully withdrawn, leading to the brief greater local application of pressure than the static load pressure of the cover on the object. Furthermore, it is extremely difficult, if not impossible, to correct the position by widening the cover again without damaging the cover or the object to be covered, for example a human organ.

In addition to the known manner of slipping an elastic cover over an object to be covered generally described above, it is also known to widen the elastic cover from the exterior using a vacuum and then to slip it over the object. For this purpose the elastic cover is briefly surrounded by a larger, rigid cover and connected to it in an airtight manner, i.e. such that there is a vacuum, which can be adjusted as desired, in the intermediate space between the elastic and the rigid covers. After positioning by slackening, the cover can be mounted over the object to be covered from the exterior by means of suited pressure adjustment without any other external influences.

For this purpose, the opening of the external, rigid cover must possess a width which at least corresponds to the largest expansion of the object to be covered. Therefore, the elastic cover must also be correspondingly widened at this point. However, this expansion cannot be obtained at the point of contact by the developing vacuum, but by mechanical gripping forces.

The elastic cover has to be expanded at the opening of the surrounding rigid cover in a conventional manner so wide that it can be attached at the edges of this opening in a suited manner, for example airtight. The attachment can, for instance, occur by means of a rubber ring. On the other hand, the opening in the rigid cover has to be at least so large that the object to be covered can pass through without using force. In this way, moreover, no complete slackening of the elastic cover is possible simply by reducing the vacuum. Therefore, it is necessary to use, at least at the point of contact, mechanical aids which suitably widen the cover.

In addition to the drawbacks described above, which also occur due to the mechanical widening, there is also the expense of complex instruments. Moreover, it is necessary, depending on the varying sizes of the objects to be covered, to employ exterior covers of varying rigidity. Finally, readjustment is not possible after removal of the exterior, rigid cover from the flexible cover.

An object of the present invention is to provide a device and a method for widening a hollow body at least partially having elastic regions, which device is connected to the hollow body and widens the hollow body to a desired circumference, in such a manner that it is possible to widen the elastic cover without mechanical influence on the interior side of this cover. Another object of the present invention is to avoid foreign bodies remaining between the cover and covered object after contraction of the elastic cover. A further object of the present invention is to provide a device and method in which the entire covering procedure is as gentle as possible for the object to be covered, and which avoids the brief exposure of local influences of force to the object to be covered.

These and other objects have been achieved by providing a device for widening a hollow body having an at least partially elastic region, including at least one elastic device connected to the hollow body, and a force transmitting means configured to stretch the elastic device in order to widen the hollow body.

These and other objects have also been achieved by providing a method of widening a hollow body having an at least partially elastic region, the method comprising the steps of attaching an elastic body to the hollow body, and stretching the elastic body with a force transmitting means in order to widen the hollow body.

The present invention provides and advantageous device and method for widening a hollow body at least partially having elastic regions, which device is connected to the hollow body and widens the hollow body to a desired circumference in such a manner that at least one elastic device which can be concertedly widened over its entire length by a force transmitting means is disposed on the hollow body.

The present invention is based on the idea to tangentially attach an elastic hose which has a closed end and an open end to the elastic hollow body suited for covering sensitive objects. A preferably flexible rod, the length of which is longer than the length of the hose which is disposed on the exterior side of the hollow body is entered into the open end of the hose. If the flexible rod is entered further into the hose than the length of the hose in the slack state permits, the elastic hose stretches over its entire length. The elastic hose is firmly connected to the walls of the hollow body along a generally circumferential course of the hollow body, such that the hollow body expands radially outward as the elastic hose stretches and assumes, in the region of the elastic hose, the widened shape of the flexible rod. The degree of widening is solely limited by the elasticity of the material and the length of the flexible rod.

Using several elastic hoses suitably disposed on or in the walls of the hollow body permits expanding the hollow body over its entire length in such manner that the objects to be protected can be covered.

In order to simplify handling of the invented expanding device for the operator, a suitable stopping and/or locking device may be provided at the open end of the elastic hose as well as at the proximal end of the flexible rod in such a manner that the elastic cover is automatically held open. Contraction of the cover can be precisely controlled by means of suitable end stopping and/or locking devices and controlled retraction of the flexible rod from the elastic hose.

It is also contemplated to expand the elastic hose disposed on the exterior side of the hollow body by concerted introduction of a gas or a liquid into the hose, requiring that the elastic hose can be made gas-tight or liquid-tight.

These and other objects, features and advantages of the present invention will become more readily apparent from the following detailed description when taken in conjunction with the accompanying drawings.

BRIEF DESCRIPTION OF THE DRAWINGS

FIG. 1b shows a longitudinal view of a slack state of the device shown in FIG. 1a;

DETAILED DESCRIPTION OF THE DRAWINGS

Figure 1A:
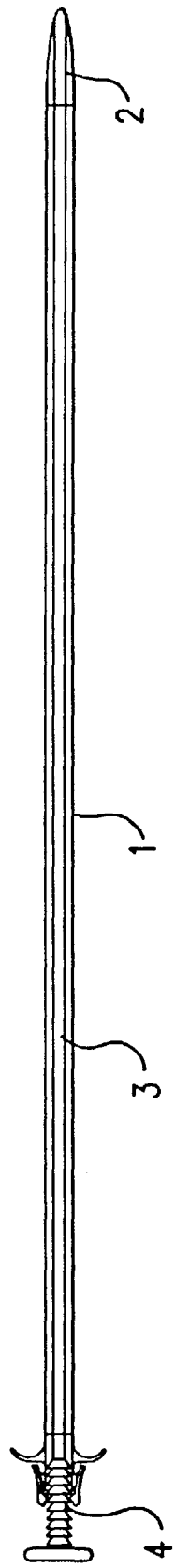
FIG. 1a shows a longitudinal view of a stretched state of a device for widening a hollow body according to a preferred embodiment of the present invention.
Figure 1B:
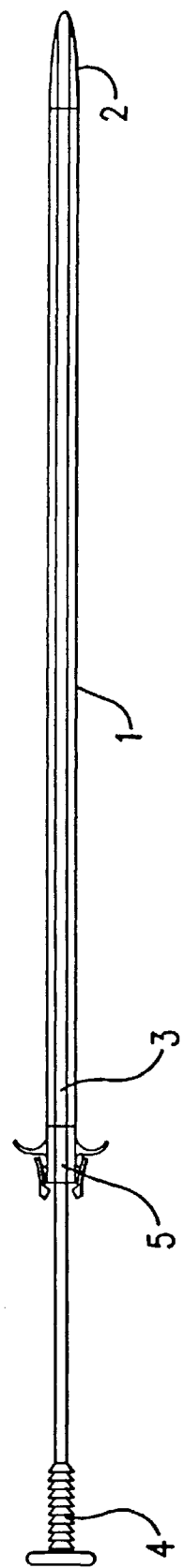

FIG. 1b shows an elastic device, in the form of an elastic hose 1, in a slack state. The elastic hose 1 has a closed end which is provided with a reinforced tip 2. The reinforced tip may be made of a fabric or a plastic material. A force transmitting means, which in this case is a flexible rod 3 which is designed solid in the longitudinal direction and flexible about the longitudinal axis, is entered into the interior of the elastic hose 1. A manipulatable and adjustable lock mechanism 4 is provided at the proximal end of the flexible rod 3. The lock mechanism 4 can be lockingly engaged with a correspondingly designed stop device 5 disposed on the open end of the elastic hose 1.

When a length of the flexible rod 3 greater than the length of the elastic hose 1 is entered into the elastic hose 1, the elastic hose is stretched lengthwise. FIG. 1a shows the expanded state of the elastic hose 1 with the flexible rod 3 completely entered into the elastic hose 1. As shown in FIG. 1a, the lock mechanism 4 provided at the proximal end of the flexible rod 3 lockingly engages with the stop device 5 to hold the elastic hose 1 in the stretched state. Although various known stop devices and lock mechanisms can be used, the lock mechanism 4 shown in the drawings is provided with teeth 8 which extend along a portion of the flexible rod 3. The teeth 8 may be extend even further in a longitudinal direction along the flexible rod than shown in the drawings, in order to provide a greater range of adjustability for locking the elastic hose 1 in varying length stretched positions, as well as for better adaptability to varying lengths of elastic hoses 1. The lock mechanism 4 in conjunction with the stop device 5 allows the elastic hose 1 to remain in a stretched position without exterior, manual influences. An essential effect of the expansion is the change in length of the elastic hose 1 from the slack state shown in FIG. 1b to the stretched state shown in FIG. 1a.

Figure 2C:
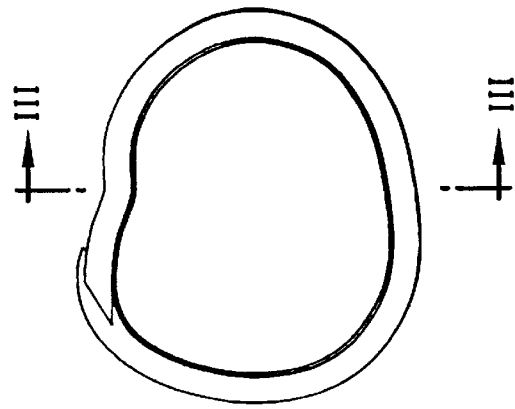
FIG. 2c shows an axial cross sectional view of a hollow body in its final position covering an object.
Figure 2B:
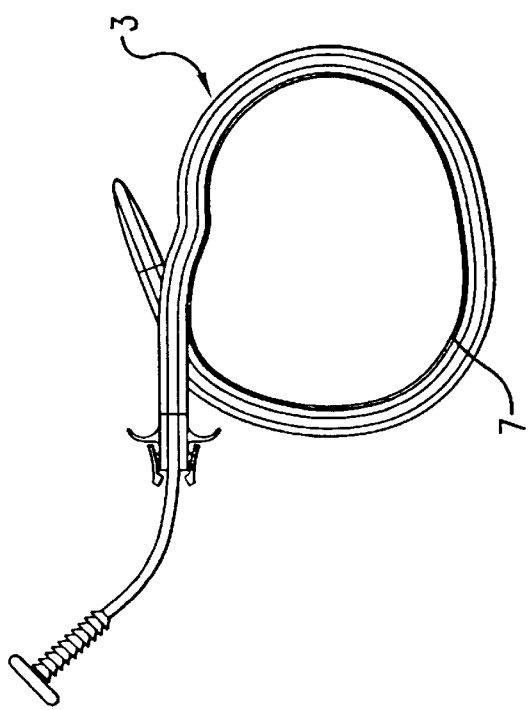
FIG. 2b shows an axial cross sectional view of a hollow body allowed to contract by the device as shown in FIG. 1a around an object.
Figure 2A:
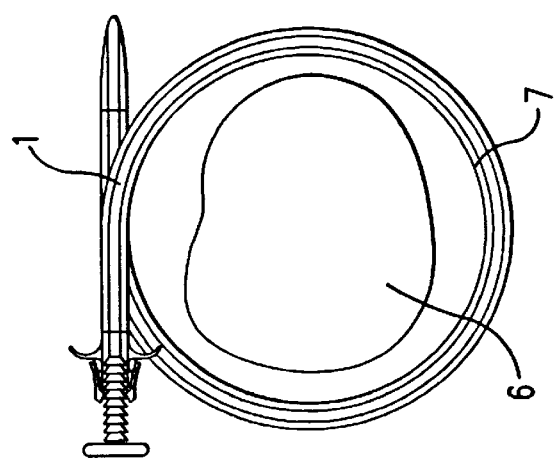
FIG. 2a shows an axial cross sectional view of a hollow body widened by the device as shown in FIG. 1a around an object.

FIGS. 2a–2c depict a practical application of the invented expanding device to cover an object 6, such as a heart.

Figure 3:
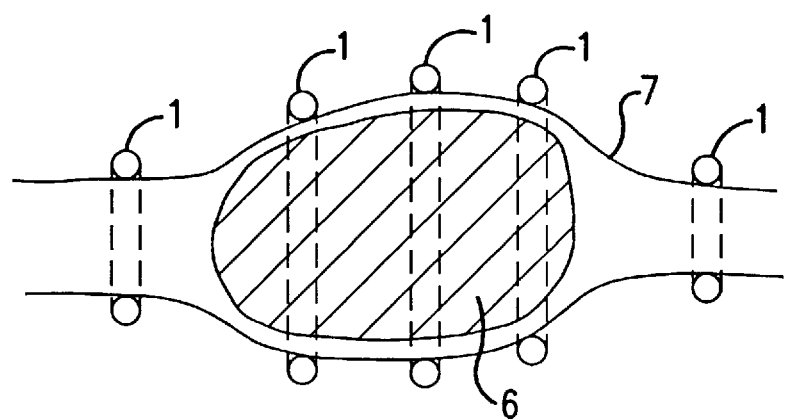
FIG. 3 shows a longitudinal cross sectional view of a hollow body covering an object, according to a preferred embodiment of the present invention.

In FIG. 2a, the expanding device is shown in the stretched state, as shown in FIG. 1a. The flexible rod 3 is completely entered into the elastic hose 1 and is retained in an expanded state by the stop device 5 which engages the lock mechanism 4. The elastic hose 1 is preferably disposed on the exterior side of the hollow body 7 in a generally circumferential course around the hollow body, which in this case is an elastic cover. The elastic hose 1 may be attached to the hollow body 7 in any appropriate known way, such as by adhesive bonding, molding, sewing, etc. only one expanding device is shown in the cross-sectional view of FIGS. 2a–2c. Of course, a multiplicity of expanding devices of the same construction can be disposed at the exterior side of the hollow body 7 in such a manner that the object 6 to be covered is completely surrounded by the hollow body 7. FIG. 3 shows a hollow body 7 having a plurality of elastic hoses 1 attached. These elastic hoses 1 can be stretched by respective flexible rods in order to widen the hollow body 7 to safely position it around the object 6 to be covered. Depending on the dimensions required, the individual elastic hoses 1 and the flexible rods 3 to be entered therein can be designed of varying length.

Once the expanded hollow body 7 has been positioned around the object 6 to be covered, as shown in FIG. 2a, the flexible rod 3 can be drawn out in a controlled manner by releasing the stop device 5, such that the hollow body 7 gently draws uniformly close to the exterior contour of the object 6 to be covered, as shown in FIG. 2b, without any jolting local pressure load.

Both ends of the elastic hose 1, i.e., the closed end 9 and the open end 10 are mechanically reinforced and themselves not tangentially connected to the hollow body 7. These ends 9, 10 may be cut off after removal of the flexible rod 3. In this manner, except for the empty piece of elastic hose 1, no other foreign bodies remain on the surface of the hollow body 7, as shown in FIG. 2c. However, if the hollow body 7 may need to be repositioned, at least the closed end 9 should not be cut off, in order to allow the flexible hose to be reinserted in the elastic hose 1 to widen the hollow body 7.

Figure 4:
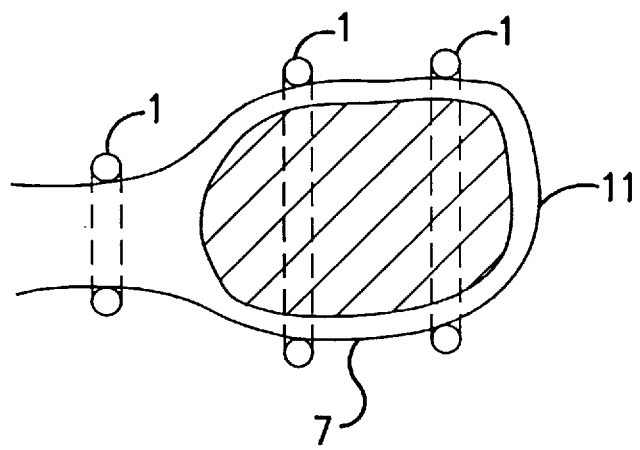
FIG. 4 shows a longitudinal cross sectional view of a hollow body covering an object, according to a preferred embodiment of the present invention.

As shown in FIG. 4, a hollow body 7 having a closed end 11 may be used.

Figure 5:
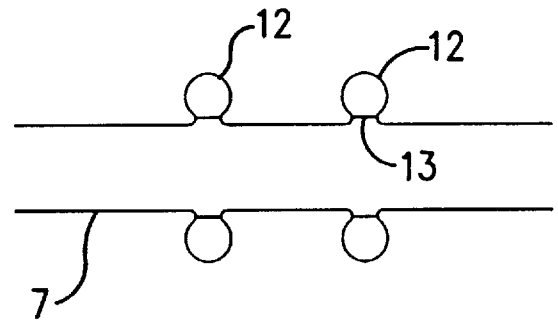
FIG. 5 shows a longitudinal cross sectional view of a hollow body covering an object, according to another preferred embodiment of the present invention.

The elastic device may comprise an integral portion of the hollow body itself, rather than a separate elastic hose attached to the hollow body. As shown in FIG. 5, the elastic device may comprise an elastic portion 12 of the hollow body 7. In this embodiment, the hollow body 7 is pushed together in a longitudinal direction such that elastic portions 12 of the hollow body 7 expand radially outwardly. Then bases of the elastic portions are connected, for example by a connection 13, in order to form the elastic device. By forming an access hole in the elastic portion 12, a force transmitting means can be entered into the elastic portion 12 to widen the hollow body 7.

Figure 6:
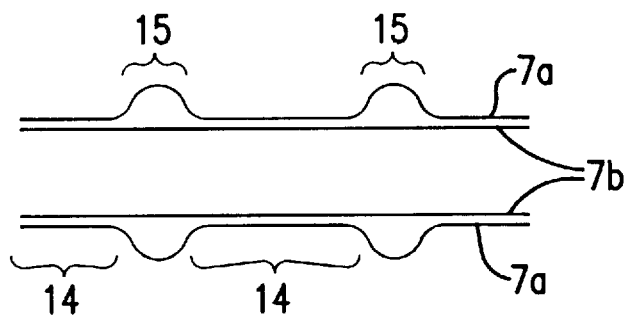
FIG. 6 shows a longitudinal cross sectional view of a hollow body covering an object, according to another preferred embodiment of the present invention.

As shown in FIG. 6, the hollow body may be formed as a multi-walled structure including an outer wall 7a and an inner wall 7b. The elastic device in this embodiment comprises portions of the walls 7a, 7b. The outer wall 7a is bonded to the inner wall 7b in portions 14. The outer wall 7a is not bonded to the inner wall 7b in portions 15. In this way, the non-bonded portions 15 form the elastic devices. By forming an access hole in the non-bonded portions 15, a flexible rod 3 can be entered into the elastic devices to widen the hollow body 7a, 7b.

Figure 7:
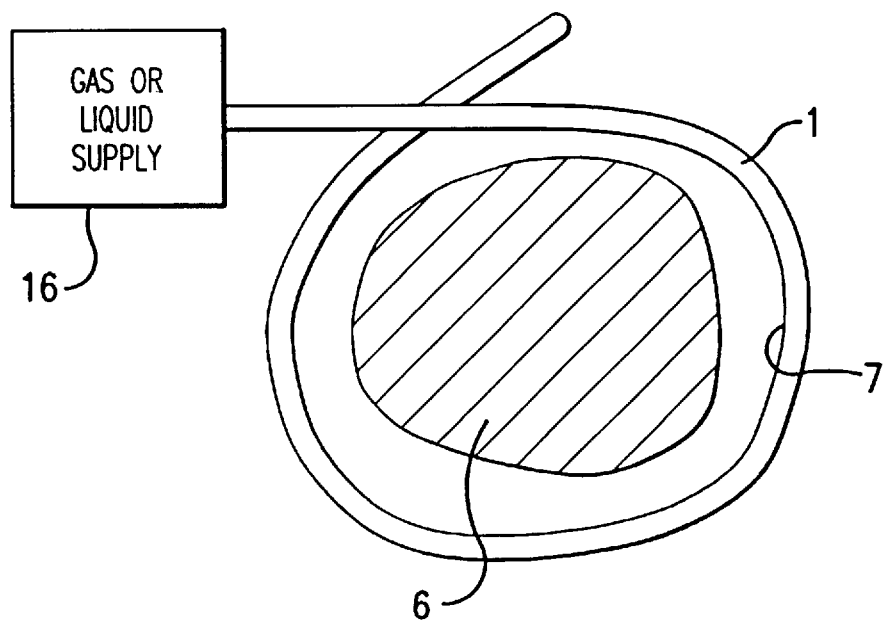
FIG. 7 shows an axial cross sectional view of a device for widening a hollow body, according to another preferred embodiment of the present invention.

As an alternative to the flexible rod 3, with a corresponding construction of the elastic hose 1, the force transmitting means may be a gas or a liquid which is entered into the hose in a controlled manner from a gas or liquid supply 16, as shown in FIG. 7. The gas or liquid is entered into the elastic hose 1 to elastically expand it and correspondingly widen the hollow body 7. Once the hollow body 7 is positioned around the object 6, the gas or liquid is withdrawn from the elastic hose 1, in order to allow the hollow body to elastically contract around the object 6. Depending on the application, one can select from available aids for elastically expanding the elastic hose.

The expanding device permits widening of an elastic cover without touching the interior, positioning the cover over an object to be covered and subsequently completely slackening it as slowly as desired. No expensive, complicated instruments are required. A particular advantage of the invented device is that widening and slackening of the cover can be repeated as often as desired as long as the corresponding end sections have not been separated respectively cut off from the cover. In this manner, if the fit of the cover on the object is not optimum, the fit can by corrected by widening and adjusting the cover, without damaging the object.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A device comprising:
   a hollow body having an at least partially elastic region;
   at least one elastic hose connected to said hollow body, said hose having an open end and a closed end; and
   a force transmitting means configured to stretch said elastic hose in order to widen said hollow body.

2. A device according to claim 1, wherein said elastic hose is connected to an exterior circumference of said hollow body by one of adhesive bonding, molding, and sewing.

3. A device according to claim 1, wherein said force transmitting means comprises a flexible rod which is configured to be insertable into said elastic hose, said flexible rod having a length which is greater than the length of the elastic hose.

4. A device according to claim 3, further comprising a stop device arranged at said open end of said hose and a lock device arranged at a proximal end of said flexible rod, said stop device being configured to engage said lock device to hold said elastic hose in a stretched position.

5. A device according to claim 1, wherein said elastic hose is elastic in a longitudinal direction, said elastic hose is connected to said hollow body with said longitudinal direction extending in a generally circumferential direction around said hollow body, and said force transmitting means is configured to stretch said elastic hose in said longitudinal direction in order to correspondingly widen said hollow body.

6. A device according to claim 1, wherein said elastic hose comprises an integral portion of said hollow body.

7. A device comprising:
   a hollow body having an at least partially elastic region;
   at least one elastic device connected to said hollow body, said elastic device being sealed in a gas-tight and liquid-tight manner; and
   a force transmitting means configured to stretch said elastic device in order to widen said hollow body, said force transmitting means being a gas or a liquid.

8. A method of widening a hollow body having an at least partially elastic region, said method comprising the steps of:
   attaching an elastic hose to said hollow body, said elastic hose having an open end and a closed end;
   stretching said elastic hose with a flexible rod in order to widen said hollow body;
   arranging a stop device at said open end of said hose; and
   arranging a lock device at a proximal end of said flexible rod, said stop device being configured to engage said lock device to hold said elastic hose in a stretched position.

9. A method according to claim 8, further comprising the steps of:
   positioning the widened hollow body around an object; and
   slackening said elastic body with said flexible rod in order to allow said hollow body to contract around said object.

10. A method according to claim 8, wherein said flexible rod has a length which is greater than the length of the elastic hose.

11. A method according to claim 8, wherein said elastic hose is elastic in a longitudinal direction, said attaching step comprises attaching said elastic hose to said hollow body with said longitudinal direction extending in a generally circumferential direction around said hollow body, and said flexible rod means is configured to stretch said elastic hose in said longitudinal direction in order to correspondingly widen said hollow body.

12. A method of widening a hollow body having an at least partially elastic region, said method comprising the steps of:
   attaching an elastic device to said hollow body, said elastic device being sealed in a gas-tight and liquid-tight manner; and stretching said elastic device by inserting a gas or a liquid into said elastic hose, thereby widening said hollow body.

13. A device comprising:

a hollow body having an at least partially elastic region;

at least one elastic body defining a channel coupled to or integral with said hollow body at said at least partially elastic region, said channel extending in a generally circumferential direction of said hollow body;

a force transmitting means insertable into said channel along said generally circumferential direction in order to stretch said elastic body and said hollow body in said generally circumferential direction.

14. A device according to claim 3, wherein said force transmitting means comprises a flexible rod which is configured to be insertable into said channel, said flexible rod having a length which is greater than the length of the channel.

15. A device according to claim 13, wherein said force transmitting means comprises a gas or a liquid.

16. A method of widening a hollow body having an at least partially elastic region, said method comprising the steps of:

one of (a) coupling at least one elastic body defining a channel to said hollow body such that said channel extends in a generally circumferential direction of said hollow body, and (b) forming a channel from said at least partially elastic region of said hollow body such that said channel extends in a generally circumferential direction of said hollow body; and inserting a force transmitting means into said channel along said generally circumferential direction in order to stretch said channel and said hollow body in said generally circumferential direction.

17. A method according to claim 16, wherein said force transmitting means comprises a flexible rod which is configured to be insertable into said channel, said flexible rod having a length which is greater than the length of the channel, and wherein said stretching step comprises inserting said flexible rod into said channel.

18. A method according to claim 16, wherein said force transmitting means comprises gas or a liquid.

* * * * *